(12) United States Patent
Timmermans et al.

(10) Patent No.: US 8,086,350 B2
(45) Date of Patent: Dec. 27, 2011

(54) DISPENSER AND METHOD FOR DISPENSING INDIVIDUAL GOODS, IN PARTICULAR PACKAGES CONTAINING A MEDICAMENT

(75) Inventors: Bartel Antonius Timmermans, The Hague (NL); Thijs van Nuenen, The Hague (NL)

(73) Assignee: Innospense Capital B.V., The Hague (NL)

( * ) Notice: Subject to any disclaimer, the term of this patent is extended or adjusted under 35 U.S.C. 154(b) by 721 days.

(21) Appl. No.: 12/239,841

(22) Filed: Sep. 29, 2008

(65) Prior Publication Data

US 2009/0084809 A1     Apr. 2, 2009

(30) Foreign Application Priority Data

Sep. 28, 2007   (EP) .................................... 07117544

(51) Int. Cl.
*G06F 17/00* (2006.01)
(52) U.S. Cl. ........ 700/242; 700/231; 700/236; 700/240; 700/244

(58) Field of Classification Search ................... 221/103; 700/231, 236, 240, 242, 244
See application file for complete search history.

(56) References Cited

U.S. PATENT DOCUMENTS

| | | | | |
|---|---|---|---|---|
| 5,600,565 A | * | 2/1997 | Wagner et al. | 700/219 |
| 5,697,519 A | * | 12/1997 | Wittern et al. | 221/76 |
| 6,199,720 B1 | * | 3/2001 | Rudick et al. | 221/6 |
| 6,415,950 B1 | * | 7/2002 | Robrechts | 221/85 |
| 6,755,322 B1 | * | 6/2004 | Herzog et al. | 221/123 |
| 7,857,161 B2 | * | 12/2010 | Pinney et al. | 700/242 |

* cited by examiner

*Primary Examiner* — Timothy Waggoner
(74) *Attorney, Agent, or Firm* — Young & Thompson

(57) ABSTRACT

Dispenser for dispensing individual goods, the dispenser comprising a containing space for holding an array of goods, a transport device for consecutively feeding a good from the array to a delivery member for dispensing one or more goods to a consumer, a reading device for reading data from a first good, a control unit connected to the reading unit for receiving data from the reading unit, the control unit being connected to a functional member and being adapted for changing the state of the functional member on the basis of the data received from the first good, characterised in that the data received from the first good includes information pertaining to one or more goods that are to be dispensed consecutively to the first good.

18 Claims, 6 Drawing Sheets

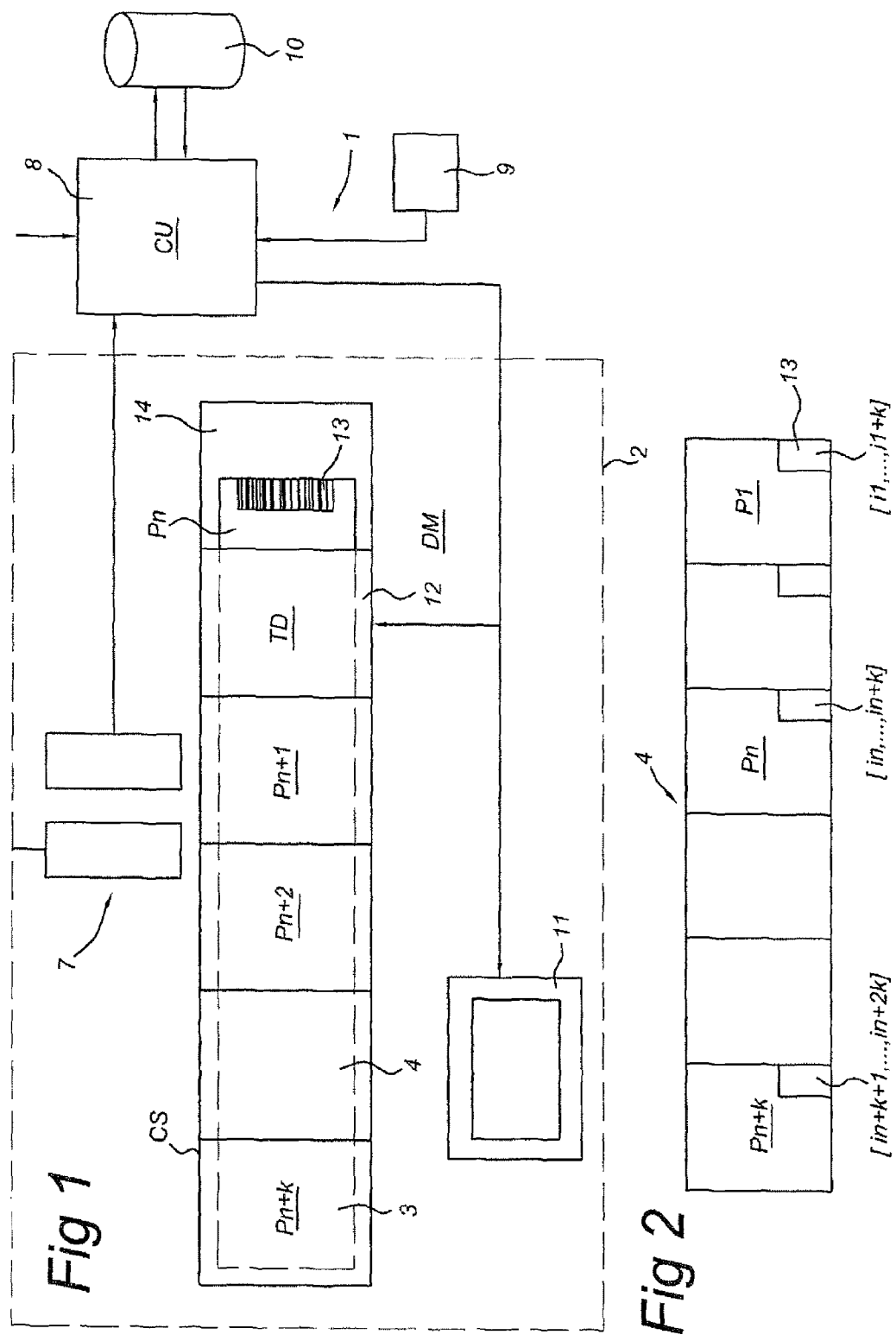

Figure 4:
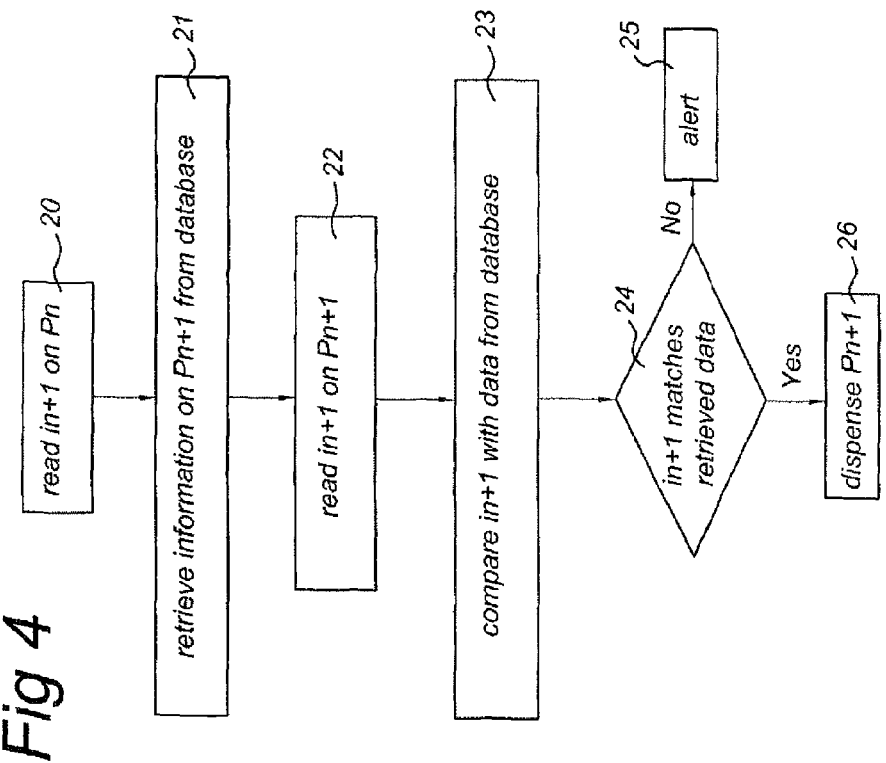

Fig 9a
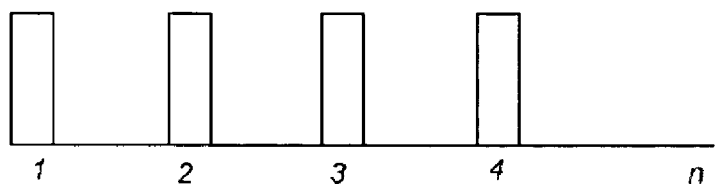
Fig 9b
Fig 10a
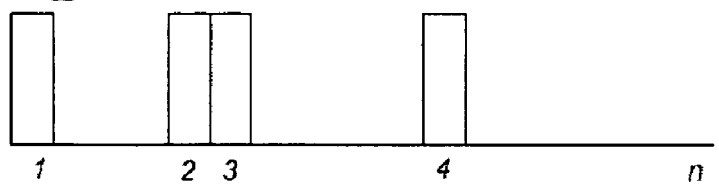
Fig 10b
Fig 11a
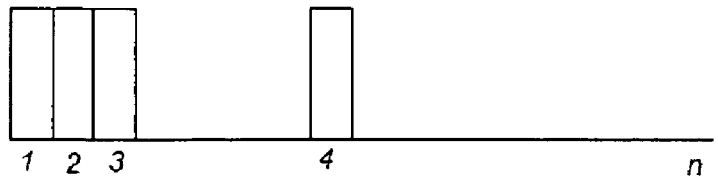
Fig 11b

DISPENSER AND METHOD FOR DISPENSING INDIVIDUAL GOODS, IN PARTICULAR PACKAGES CONTAINING A MEDICAMENT

Dispenser and method for dispensing individuals goods, in particular packages containing a medicament.

The invention relates to a dispenser for dispensing individual goods, the dispenser comprising a containing space for holding an array of goods, a transport device for consecutively feeding a good from the array to a delivery member for dispensing one or more goods to a consumer, a reading device for reading data from a first good, a control unit connected to the reading unit for receiving data from the reading unit, the control unit being connected to a functional member of the dispenser and being adapted for changing the state of the functional member on the basis of the data received from the first good.

The invention also relates to a method of dispensing and to a good, in particular an individually packed medicament, and to an array of such goods for use in a dispenser according to the invention.

Such a dispenser is known from U.S. Pat. No. 5,700,998. This patent describes coding of drug pills with a machine readable code including name and dosage of the pill. Prior to dispensing of a pill, each pill is scanned and the data is compared with a drug delivery information file relating to a particular patient. An alarm is generated if a discrepancy is detected between the pill identification information and the desired drug delivery information.

It is an object of the present invention to provide a dispenser of the above described type and a method of dispensing, in which a fail-safe dispensing can be carried out in a flexible manner while using relatively little computer memory. It is a further object of the present invention to provide a dispenser and method of dispensing, in which a relatively long time interval is available for the dispenser to communicate with a remote data base. It is again an object of the invention to provide a dispenser and method of dispensing in which an operator has sufficient time to react on an indication, such as an alarm, generated during dispensing.

Hereto the dispenser according to the invention is characterised in that the data on the first good includes information pertaining to one or more goods that are to be dispensed consecutively to the first good.

By obtaining information about consecutive goods $P_{n+1} \ldots P_{n+k}$ that are to be dispensed following dispensing of a particular good $P_n$ from the good $P_n$, the dispensing of the consecutive goods is anticipated. Hereby time becomes available for dispensing of the consecutive product, for checking the consecutive product with data read from the consecutive product itself upon dispensing, and/or for making a check with a central database prior to dispensing of the consecutive good. For instance, it is possible to verify the number, k, of the of consecutive goods $P_{n+1} \ldots P_{n+k}$ that are to be dispensed within a specific timeframe following dispensing of good $P_n$ or to retrieve properties of the consecutive goods from a database, such as dosage, composition, user (patient) data, application data, type numbers, etc. Hereby, prior to dispensing good $P_{n+1}$, it is already known which number and which type of goods is to be expected, at a specific time of dispensing. When the consecutive good $P_{n+1}$ is actually dispensed, the data $(i_{n+1})P_{n+1}$ pertaining to this consecutive good $P_{n+1}$ can be detected from this good and compared to the pre-processed information $(i_{n+1})P_n$ that was obtained from the earlier good $P_n$ (or from any other earlier dispensed good $P_{n-1}$). When a discrepancy occurs, an alarm may be generated, alerting an operator or a data entry may be made into an electronic dispensing log or user (patient) file. In this way a reliable and fail-safe dispensing is obtained.

The dispenser and method of dispensing according to the present invention may result in a simple manner in a versatile dispensing regime, in which following on dispensing a good $P_n$, a specific time interval may be generated after which good $P_{n+1}$ is dispensed. Each good may generate a specific dispensing time after which the next object is dispensed. Furthermore, for instance, each good $P_n$ may generate immediate consecutive dispensing of k consecutive goods, for instance oral dosages of vitamins or medicaments, which should be ingested by a person simultaneously or in quick succession. In this way a relatively complex dispensing sequence may be obtained without storing each dispensing time in a computer memory.

In one embodiment of the dispenser of the present invention uses the data $(i_{n+1} \ldots i_{n+k})P_n$ received from the first good $P_n$ for retrieving from a database the information of one or more goods $P_{n+1} \ldots P_{n+k}$ that are to be dispensed consecutively to the first good $P_n$. Based on the retrieved data from the database and the data $(i_{n+1} \ldots i_{n+k})P_{n+k}$ read from the good $P_{n+kn}$ prior to dispensing, a control command based on the comparison can be generated, such as generation of an alarm, a drive signal for a transport member initiating the dispensing and the like.

By obtaining information $(i_{n+1} \ldots i_{n+k})$ from the good $P_n$ that is dispensed, which information relates to consecutive goods $P_{n+1} \ldots P_{n+k}$ that are to be dispensed, the dispenser has sufficient time to communicate with a remote database, such as via a wired connection (electrical or optical) or via a wireless connection (Bluetooth, wifi) or an infrared communication port. Hereby sufficient time is available for roaming and hand shaking, transmission of entry codes, encryption, establishing and verifying the connection and for data transmission and retrieval from a remote database, for instance via internet access. When the control command is in the form of an alarm which is generated at the moment of dispensing good $P_n$, for instance when good $P_{n+1}$ is missing or is of the wrong type, more time is available for an operator to act than in case the alarm is generated only at the time of dispensing of good $P_{n+1}$.

The functional member on the dispenser may comprise an automatic transport or feed system that is driven by the control command in dependence of the information detected upon dispensing of a good. The transport or feed system may in case of a discrepancy between the expected data read from good $P_n$ and detected data from good $P_{n+k}$ be interrupted to prevent dispensing. Alternatively, or in addition, the functional member comprises an indicator such as an acoustical indicator or an optical indicator such as a LED, a mechanical indicator turning a window red or green, or a display (LCD, TFT-display) indicating the type, product information and time of dispensing of the consecutive goods. It is also possible that only an indication is provided of type, number and time of dispensing, the actual dispensing being carried out by hand by an operator or user.

The dispenser of the present invention may be used for dispensing a variety of goods, such as food products (candy bars, drinks cans or bottles), machine parts from a store, plant food in sachets, production parts in an assembly line, etc.

The dispenser and method of the dispensing is particularly suitable for dispensing individually packed goods, such as vitamins or medicaments. These vitamins or medicaments may be packed in strips of interconnected individual packages such as described in international patent application no. PCT/NL2006/050305 in the name of the applicant. These strips of interconnected packages can be stored in the dispenser in a meandering manner. The product, user and/or dispensing information may be printed on the each package in a machine readable code (such as a two-dimensional bar code) or provided on each package by a RFID (radio frequency identification) tag, a microchip or any other suitable data carrier.

In a further embodiment of a dispenser according to the present invention, the control unit counts and stores the number of packages being dispensed and generates an order command after a pre-determined number of packages have been dispensed. In this way, the dispenser can at a timely moment be restocked with fresh goods to be dispensed with a minimum down time due to the dispenser running empty.

In again another embodiment of a dispenser according to the present invention, the dispenser comprises an input device for receiving comprising for instance the total number of packages contained in the dispenser assembly, the dispensing time interval between dispensing of consecutive packages or a dispensing termination date.

In this manner, the input device can detect from a general package of the goods to be dispensed, a label or other data carrier, general product information that is not stored on each good to be dispensed. In this way the control unit may be pre-programmed in a general manner, suitable for the type of goods that are dispensed, whereas the individual dispensing is carried out on the basis of data present on each individual good.

Figure 3:
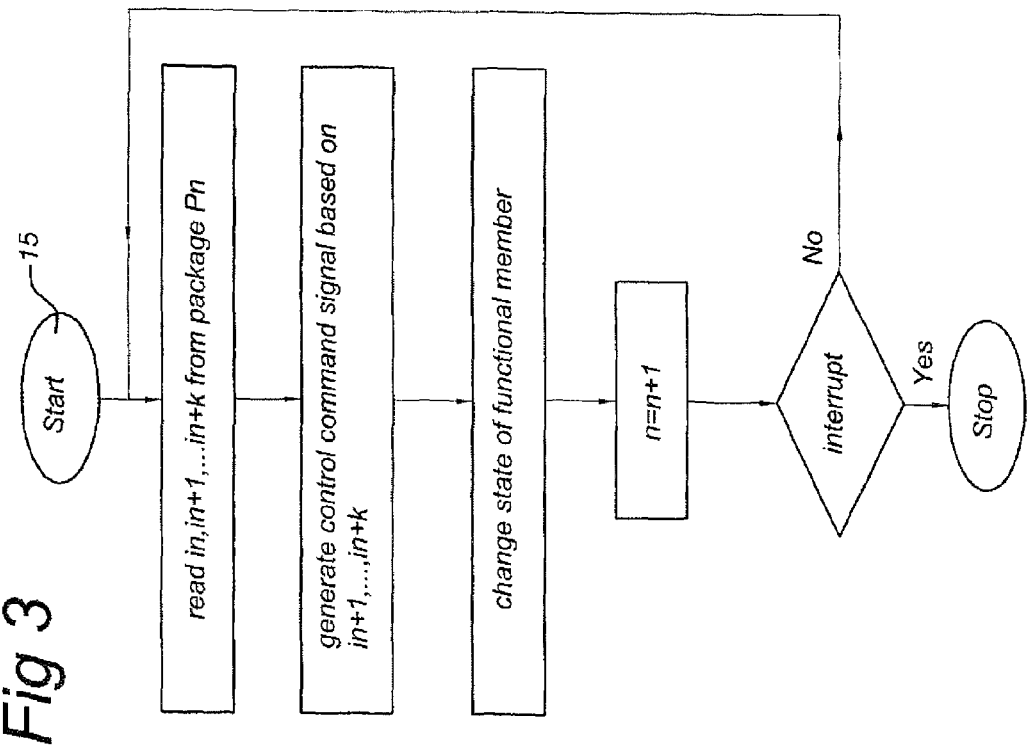
Figure 5:
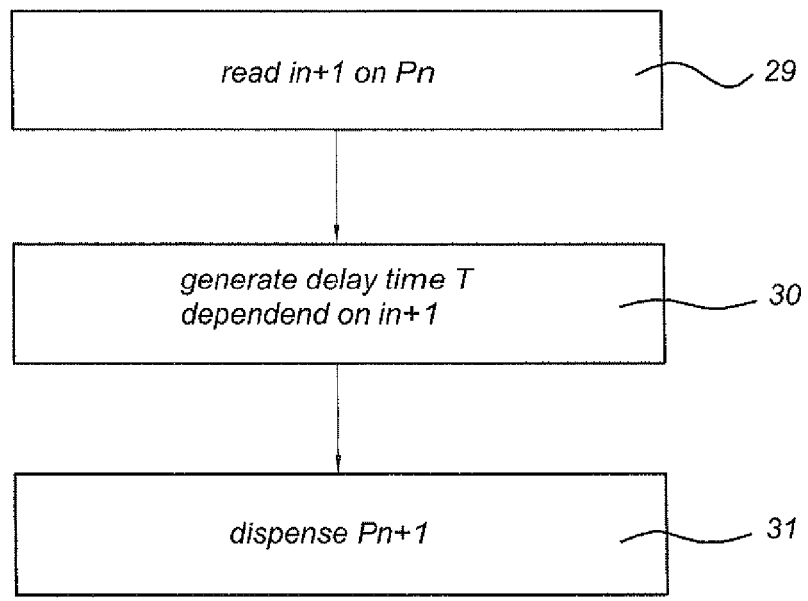
Figure 6:
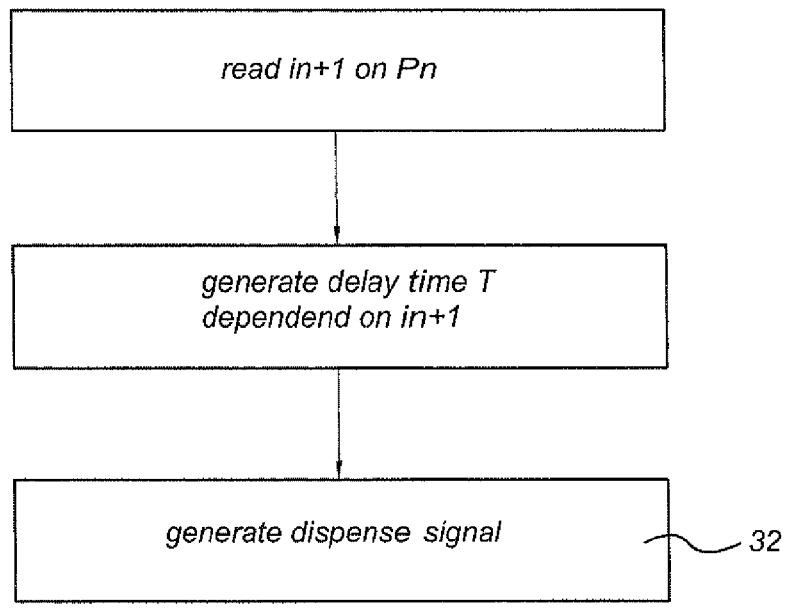
Figure 7:
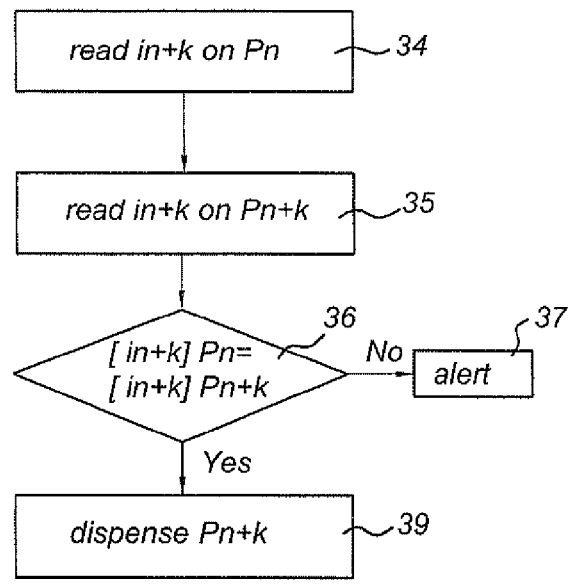
Figure 8:
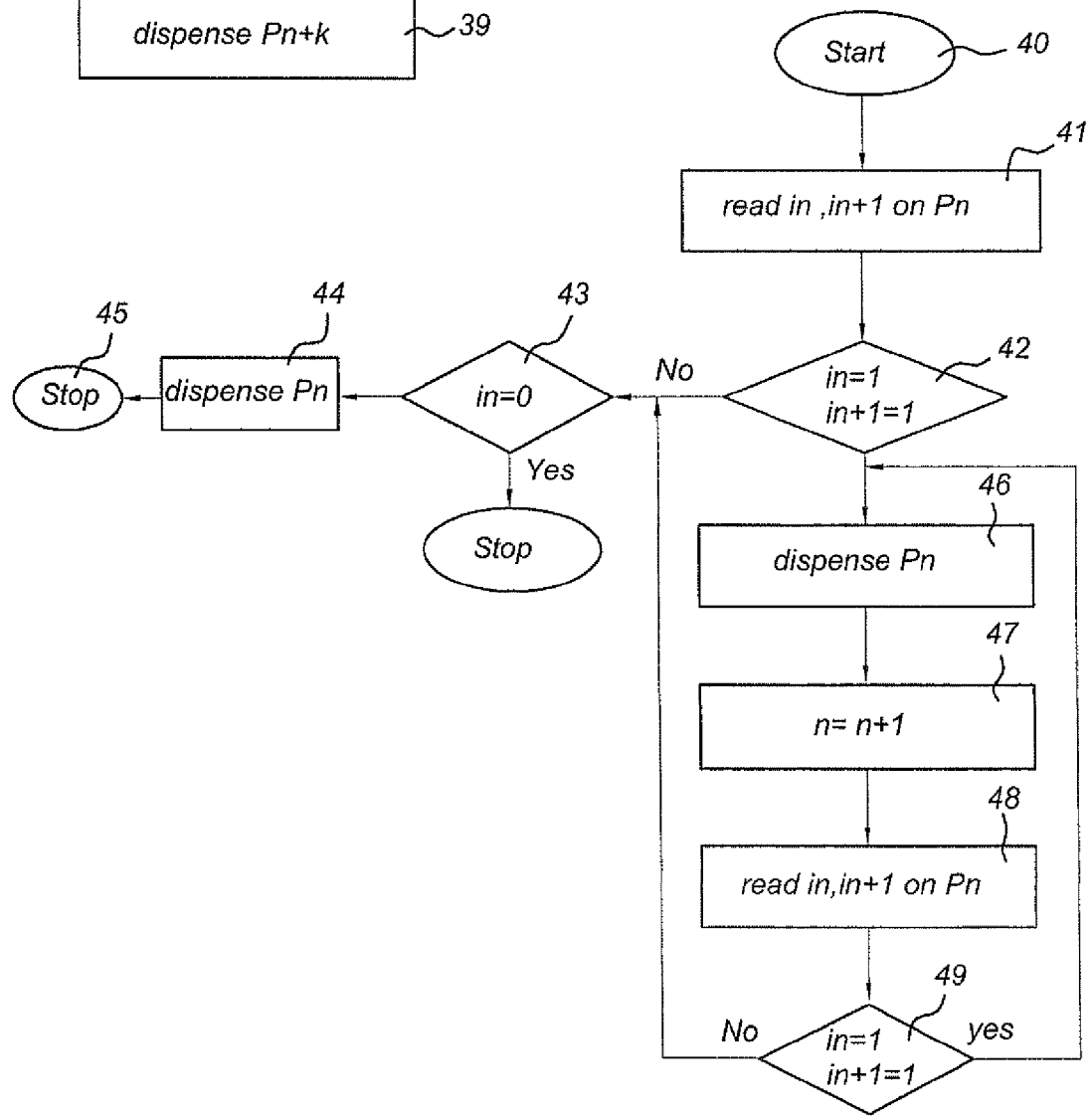
Figure 12:
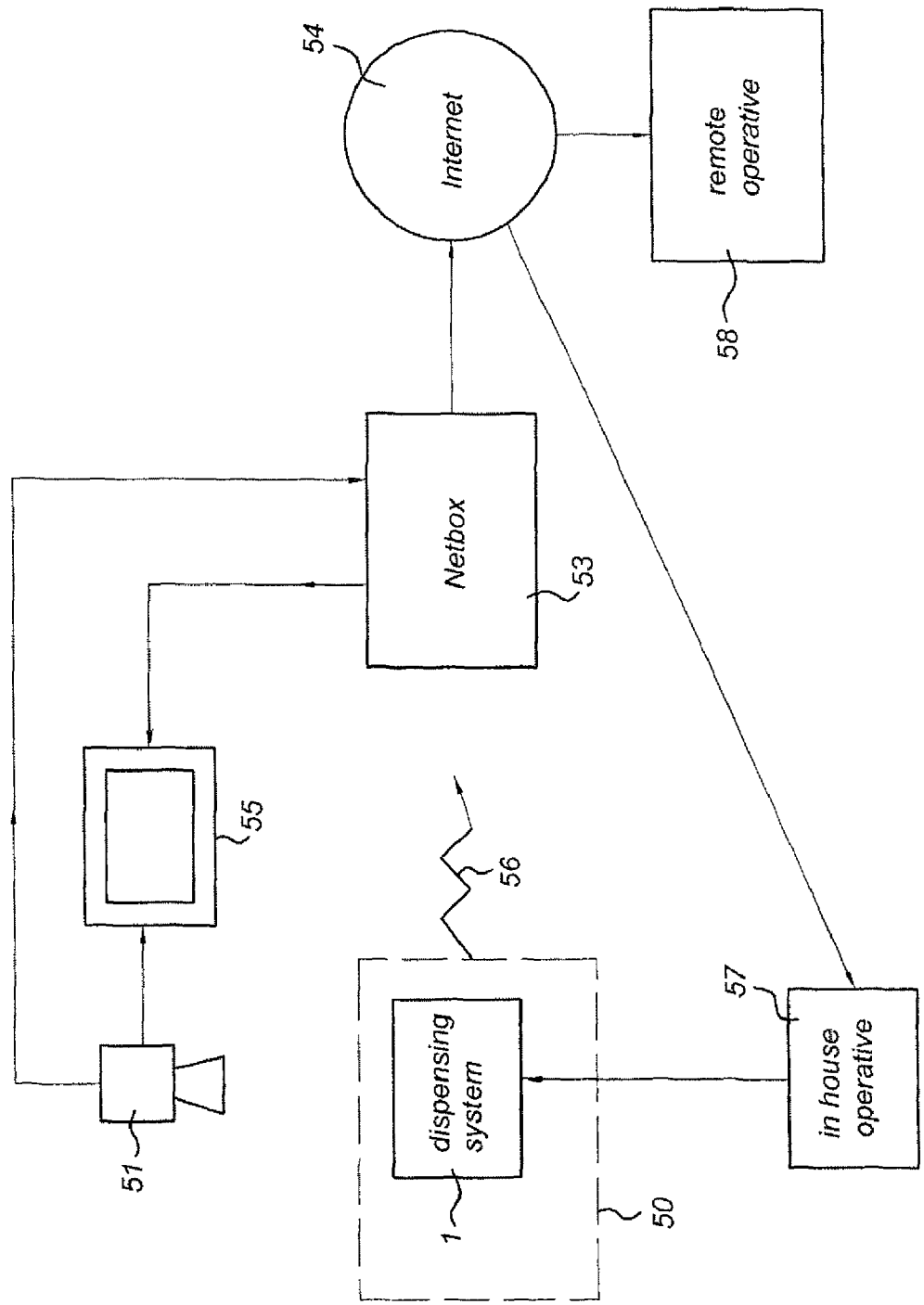

Some embodiments of the dispensing system and method of dispensing according to the invention will by way of example be explained in detail with reference to the accompanying drawings. In the drawings:

FIG. 1 shows a schematic lay-out of the system for dispensing of medicaments contained in an array of packages according to the invention, FIG. 2 shows an example of a strip of interconnected individually packed medicaments, in which each package contains information about one or more consecutive packages, FIG. 3 shows a schematic flow chart of the operation of the system of FIG. 1, FIG. 4 shows an embodiment in which information for product $P_{n+1}$ is retrieved from a remote database after reading data $i_{n+1}$ on product $P_n$, for generating the command control signal, FIG. 5 shows an embodiment in which a delay time T after dispensing product $P_n$ is generated as a command control signal, prior to dispensing of product $P_{n+1}$, FIG. 6 shows an embodiment of the type as shown in FIG. 5 for manual dispensing of the medicaments, FIG. 7 shows an embodiment in which data $i_{n+k}$ pertaining to the $k^{th}$ consecutive product $P_{n+k}$ is read from product $P_n$, and is compared with data read from product $P_{n+k}$, FIG. 8 shows an embodiment in which dispensing of a consecutive product $P_{n+1}$ is generated by reading simple dispensing data on product $P_n$, FIGS. 9a, 9b, 10a, 10b, 11a and 11b show different dispensing sequences that are possible using the simple product coding of FIG. 8, and FIG. 12 shows the lay-out of the system incorporating the dispensing system of the present invention especially suitable for application in a home for the elderly or a hospital.

In FIG. 1, a dispensing system 1 is shown with a dispenser 2 having a container 3 with a containing space CS in which a folded-over strip 4 of individually packed medicaments is placed. Each package $P_n$ contains information pertaining to the package itself and to one or more consecutive packages $P_{n+1} \ldots P_{n+k}$. The information may be in the form of visual indicia, such as a one or two-dimensional bar code, or may be present in electronic form for instance on a microchip or on an RFID tag. In FIG. 1, product $P_n$ is shown projecting from the container 4 and being transported by transport device 12 to a delivery member 14, the product $P_n$ being provided with optical indicia in the form of a one dimensional bar code 13.

A reading device 7 is provided for detecting the information on each package $P_n$ prior to dispensing. The reading device 7 may have the form of an optical scanner, a remote reader for microchips, a RFID detector, a digital camera, or other generally known detection devices. The output of the reading device 7 is connected to a control unit 8 either via an electrical or optical line or via a wireless link. In the control unit 8, the data $i_{n+k}$ from the packages $P_n$ is processed, for instance by using the data $i_{n+1}$ derived from package $P_n$ for retrieving information about package $P_{n+1}$ from a database 10.

In the control unit 8, a control command signal is formed, based on the data $i_{n+1}$ derived from package $P_n$. This control command signal may be a drive signal that is input to the transport device 12 of the container 3 for dispensing package $P_{n+1}$ to a delivery member 14, which delivery member may comprise an aperture in the container 4 or a receiving tray. Alternatively, or in addition, the control command signal is input to a display device 1 for indicating information about the product Pn+1, such as the upcoming dispensing moment, type, dosage or composition.

A preferred strip of individually packed medicaments and a dispenser for dispensing these individually packed medicaments is described in International Patent Application no. PCT/NL2006/050305 in the name of the applicant, which is incorporated herein by reference. The invention can however also be practised with other arrays of food products that are to be dispensed consecutively, such as a vertical or horizontal stack of pouches, coffee or tea pads, a cartridge containing pills, wherein each pill has at its surface data (e.g. printed, etched or engraved) pertaining to one or more consecutive pills in the cartridge, and the like.

In FIG. 2 a schematic view is shown of the strip 4 of interconnected pouches $P_1$-$P_{n+k}$. Each pouch $P_n$ is provided with an information carrier 13 that comprises data pertaining to the pouch $P_n$ itself and additional data $i_{n+1}$ pertaining to the next consecutive pouch. It is possible to store on one pouch $P_n$ data $i_{n+1} \ldots i_{n+k}$ of k consecutive pouches. Hence by reading out information carrier 13 on pouch $P_n$, information is obtained about the pouch $P_n$ itself and about the k consecutive pouches, such as composition, time of dispensing or dosage regime, active substance, authentication code, production lot, distributor information, end user information, last possible date of use, and the like.

In FIG. 3, the general operation of the dispensing system 1 of FIG. 1 is shown. In step 15 a user generates a dispensing command to the control unit 8, for instance via input terminal 9. The input terminal may have the form of a push button on the dispenser 2 or can be formed by a remote terminal which is operated by another person than the users such as for instance a nurse. Upon receiving the start signal, the control unit 8 activates the reading device 7 for reading the data carrier 13 on the package $P_n$ and for obtaining data $i_{n+1}$-$i_{n+k}$ for the next consecutive k packages to be dispensed.

The data of the packages $i_{n+1}$-$i_{n+k}$ is stored in the control unit 8 and may be compared with information pertaining to pouches $P_{n+1}$-$P_{n+k}$ that is retrieved from database 10 in the time when pouch $P_n$ is being transported by the transport device 12 to the delivery member 14 for use.

When the data retrieved from the database 10 matches the data $i_{n+1}$-$i_{n+k}$, a control command signal is generated for changing the state of the functional member, which may be formed by transport device 12, by an indicating device 11 or the like. The control command may cause the transport device to dispense one or more packages $P_{n+1} \ldots P_{n+k}$, after a predetermined delay time or may indicate the next moment of dispensing on indicating device 11.

When the data $i_{n+1}$ does not match the data retrieved from the database 10, an interrupt signal is generated in the control unit 10 and dispensing is blocked. An alert may in such a case be generated on a central monitoring system.

In an alternative system, a security check is carried out by comparing the data $i_{n+1}$ for upcoming package $P_{n+1}$, which data is detected by scanning package $P_n$, with the data ink that is detected on the upcoming package $P_{n+1}$ itself. When these data are not identical, this indicates that the sequence of medicaments has been disturbed, possibly by human error or tampering, and that one or more packages $P_{n+1}$ have been interchanged or are missing. Again, dispensing can be interrupted by blocking the dispenser and a warning signal may be generated.

In again an alternative system, the data on a package $P_n$ may be indicative for driving or blocking the transport device 12. By providing on a package a simple indication such as 1 or 2 bars, a varying dispensing sequence can be obtained by placing a number of 1-bar pouches or two-bar pouches in sequence, as will be explained hereafter in relation to FIGS. 8 to 11.

FIG. 4 shows an embodiment in which the control unit 8 uses the time in which the product $P_n$ is dispensed to access the database 10 and to retrieve data for the product $P_{n+1}$ in step 21. The database 10 is accessed on the basis of the data $i_{n+1}$ that is read from the product $P_n$ in step 20. This data retrieved from the database is compared with the data $i_{n+1}$ that is read in step 22 from the subsequent product $P_{n+1}$ that is to be dispensed in step 23. A check is made in step 24 if the data $i_{n+1}$ matches the retrieved data. If this is so, the product $P_{n+1}$ is dispensed in step 26. if this is not so, an alert signal is generated in step 25.

In the embodiment of FIG. 5, the information $i_{n+1}$ that is read from the product $P_n$ in step 29 is used in step 30 to generate a delay time $T(i_{n+1})$ for the specific package $P_{n+1}$. After the delay time $T(i_{n+1})$, which is set based on the data $i_{n+1}$ retrieved from the product $P_n$, the product $P_{n+1}$ is dispensed by operation of the transport device 12. As shown in FIG. 6, the same dispensing regime may be obtained using manual dispensing, by activating in step 32 an optical or acoustical dispense signal after passing of the delay time $T(i_{n+1})$, following which a user may manually dispense a medicament from the dispenser 2.

In the embodiment shown in FIG. 7, the data $i_{n+k}$ for the next k-subsequent package $P_{n+k}$ is read from package $P_n$. Prior to dispensing package $P_{n+k}$, the data $i_{n+k}$ is read from the package $P_{n+k}$ in the step 35. This data is compared in step 36 with data $i_{n+k}$ that is read from package $P_n$ and an alert is generated if the data do not match. If for the data read from package $P_n$ and from package $P_{n+k}$ holds: $(i_{n+k})P_n=(i_{n+k})P_{n+k}$ then in step 39 the product $P_{n+k}$ is dispensed.

In the embodiment shown in FIG. 8, a varying time sequence of packages may be dispensed in a grouped or in an equally spaced manner. As is shown in FIG. 9, each package $P_n$ comprises two digits, the first digit indicating data about the dispensing of package $P_n$, the next digit comprising data about dispensing of the next package $P_{n+1}$. The indicica on package $P_n$ are read. If the first digit on a package $P_n$ is a 0, no dispensing occurs. This may for instance be desirable in the package $P_n$ is the last package in an array to be dispensed, and that instead of dispensing package $P_n$ an order signal for a refill of packages is generated. If the first digit on package $P_n$ is in the form of a "1", and the second digit is a 0, only package $P_n$ is dispensed, whereafter the dispensing cycle is stopped. If the first digit on $P_n$ is a 1 and the second digit is a 1, package $P_n$ is dispensed and the cycle is repeated for next package $P_{n+1}$.

The programming according to the algorithm of FIG. 8 in combination with the array of package shown in FIG. 9a, leads to a dispensing sequence as shown in FIG. 9b, for packages $P_1, P_2, P_3$ and $P_4$. As can be seen, the packages $P_1$-$P_4$ are dispensed at equally spaced time intervals.

If the data on the array of packages is as shown in FIG. 10a, packages $P_2$ and $P_3$ are dispensed in immediate succession, one after the other, at equal time intervals following on package P1 and preceding package $P_4$. This is for instance advantageous is packages $P_2$ and $P_3$ contain a combination doses of medicaments of food products which need to be ingested simultaneously.

If the data on the array of packages $P_n$ is as shown in FIG. 11a, the packages $P_1, P_2$ and $P_3$ are dispensed in rapid succession, followed by delayed dispensing of package $P_4$.

The data on the packages $P_n$ in FIGS. 9-11 can be in the form of alpha-numerical code, an optically readable code (such as a bar code), dots, single bars, and the like. Using a simple bar code, 1 bar may correspond to code 10 and signify dispensing Package $P_n$, 2 parallel bars may correspond to code 11 and signify dispensing $P_{n+1}$ and 3 parallel bars may correspond to code 00 and signify non-dispensing.

FIG. 12 shows a network in which the dispensing system 1 of the present invention is incorporated. The dispensing system 1 is for instance installed in a house for the elderly at a user location 50. A camera 51 observes the user location 50 and sends its information to interface 53, such as a set-top box, or communication module that is attached to the internet 54.

A monitor 55, that may be located outside the user location 50, for instance in a local control room or on a corridor along which several user locations 50 are situated, is connected to the camera 51 for displaying the user location, or a part thereof. The dispensing system 50 is via a wireless connection 56 connected to the interface 53. Data generated by the dispensing system 1 may be displayed on the monitor 55, such as alerts, moments of dispensing, information about the product that is dispensed, and the like. Via the internet 54, the data from the dispensing system 1 and from the camera 51 may be provided to an in-house operative at a central control location 57 monitoring several sets of user locations. Alternatively, the data from the dispensing system are relayed to a remote operative 58 which may be at another site, or at a supplier site, for supplying additional medicaments if the dispensing system 1 generates a corresponding command.

The invention claimed is:

1. Dispenser (2) for dispensing individual goods ($P_1 \ldots P_n$), the dispenser comprising a containing space (CS) for holding an array $[P_1 \ldots P_{n+k}]$ of goods, a transport device (12) for consecutively feeding a good ($P_n$) from the array $[P_1 \ldots P_{n+k}]$ to a delivery member (14) for dispensing one or more goods to a consumer, a reading device (7) for reading data from a first good ($P_n$), a control unit (8) connected to the reading unit (7) for receiving data from the reading unit, the control unit (8) being connected to a functional member (11,12) and being adapted for changing the state of the functional member (11, 12) on the basis of the data received from the first good, characterised in that the data $(i_{n+1} \ldots i_{n+k})P_n$ received from the first good ($P_n$) includes information pertaining to one or more goods ($P_{n+1} \ldots P_{n+k}$) that are to be dispensed consecutively to the first good ($P_n$).

2. Dispenser (2) according to claim 1, wherein the reading unit (7) obtains data $(i_{n+k})P_{n+k}$ pertaining to the consecutive good $(P_{n+}k)$ from the consecutive good $(P_{n+k})$, which data is input into the control unit (8) that compares the data $(i_{n+k})P_{n+k}$ read from the consecutive good $(P_{n+k})$ with the data $(i_{n+k})P_n$ pertaining to the consecutive good $(P_{n+k})$ that was derived from the first good $(P_n)$, and generates a control command based on the comparison.

3. Dispenser (2) according to claim 1, wherein the control unit (8) uses the data $(i_{n+1} \ldots i_{n+k})P_n$ received from the first good $(P_n)$ for retrieving from a database (10) the information of one or more goods $(P_{n+1} \ldots P_{n+k})$ that are to be dispensed consecutively to the first good $(P_n)$.

4. Dispenser (2) according to claim 1, wherein the goods $(P_1 \ldots P_n)$ comprise individually packed objects, in particular medicaments, each object being contained in a package.

5. Dispenser (2) according to claim 1, wherein the functional member comprises the transport device (12) which is driven to dispense at least a consecutive good $(P_{n+k})$ after a predetermined time period (T) following on the dispensing of a first good $(P_n)$.

6. Dispenser (2) according to claim 1, wherein the functional member comprises an indicating unit (11), indicating information pertaining to the at least one consecutive good $(P_{n+k})$.

7. Dispenser (2) according to claim 5, wherein the indicating (11) unit is adapted for indicating the moment of dispensing of at least the consecutive good $(P_{n+k})$.

8. Dispenser (2) according to claim 1, the control unit (8) being adapted for activating the transport device (12) to dispense a predetermined number of goods $(P_{n+1} \ldots P_{n+k})$ after dispensing the first good $(P_n)$.

9. Good $(P_n)$, for use in a dispenser (2) according to claim 1, comprising data $(i_{n+k})P_{n+k}$ pertaining to at least one consecutive good $(P_{n+k})$ for use in the array of goods $[P_1 \ldots P_{n+k}]$, which consecutive good $(P_{n+k})$ is to be dispensed at a later moment in time.

10. Array $[P_1 \ldots P_{n+k}]$ of goods according to claim 9, each good $(P_n)$ being comprised in a respective package, the packages forming the array and being arranged for consecutive dispensing from the dispenser, each leading package $(P_n)$ comprising data $(i_{n+k})P_n$ pertaining to one or more following packages $(P_{n+k})$ that are arranged for dispensing at a later moment in time.

11. Array $[P_1 \ldots P_{n+k}]$ according to claim 10, the array comprising a strip (14) of interconnected packages.

12. Array $[P_1 \ldots P_{n+k}]$ according to claim 10, the array comprising information for controlling operation of the dispenser.

13. Method of dispensing individual goods $(P_1 \ldots P_n)$, comprising the steps of:
consecutively dispensing the goods from an array $[P_1 \ldots P_{n+k}]$ of goods via a dispenser (2),
detecting data $(i_{n+k})P_n$ on a leading good $(P_n)$, the data pertaining to at least one consecutive good $(P_{n+k})$ followed or preceded by
dispensing of the leading good $(P_n)$, and
changing the state of a functional member (11,12) on the dispenser on the basis of the data $(i_{n+k})P_n$ received from the leading good $(P_n)$ prior to or upon dispensing of the consecutive good $(P_{n+k})$.

14. Method according to claim 13, wherein a reading unit (7) obtains data $(i_{n+k})P_{n+k}$ pertaining to the consecutive good, from the consecutive good $(P_{n+k})$, which data is input into the control unit (8) that compares the data $(i_{n+k})P_{n+k}$ read from the consecutive good $(P_{n+k})$ with the data $(i_{n+k})P_n$ pertaining to the consecutive good and read from the first good $(P_n)$, and generates a control command based on the comparison.

15. Method according to claim 13, comprising the step of using the data $(i_{n+1} \ldots i_{n+k})P_n$ received from the first good $(P_n)$ for retrieving from a database (10) the information pertaining to one or more goods $(P_{n+1} \ldots P_{n+k})$ that are to be dispensed consecutively to the first good $(P_n)$.

16. Method according to claim 13, the goods $(P_1 \ldots P_n)$ comprising individually packed goods, in particular medicaments.

17. Method according to claim 13, wherein the data $(i_{n+k})P_n$ on the leading good comprises a delay time, the delay time being communicated to an operator acting on the goods for dispensing, wherein a consecutive good $(P_{n+k})$ is dispensed by the operator after said delay time.

18. Method according to claim 13, wherein the data $(i_{n+k})P_{n+k}$ is input into an indicating device (12) and information about at least the consecutive good $(P_{n+k})$ is communicated via said indicating device.

* * * * *